United States Patent [19]
Lyttle et al.

[11] Patent Number: 5,880,097
[45] Date of Patent: Mar. 9, 1999

[54] TETHERED PRODRUGS

[75] Inventors: Matthew H. Lyttle, Point Reyes Station; Lawrence M. Kauvar, San Francisco, both of Calif.

[73] Assignee: Terrapin Techologies, Inc., South San Francisco, Calif.

[21] Appl. No.: 582,966

[22] Filed: Jan. 4, 1996

[51] Int. Cl.$^6$ .............................. A61K 38/00; C07K 5/23
[52] U.S. Cl. .............................................. 514/18; 530/331
[58] Field of Search ................................ 530/331; 514/18

[56] References Cited

U.S. PATENT DOCUMENTS

| | | | |
|---|---|---|---|
| 5,545,621 | 8/1996 | Kauvar et al. | 514/18 |
| 5,556,942 | 9/1996 | Kauvar et al. | 530/331 |

FOREIGN PATENT DOCUMENTS

| | | |
|---|---|---|
| 0 163 500 | 5/1985 | European Pat. Off. . |
| 0 420 121 | 9/1990 | European Pat. Off. . |
| WO 95 08563A | 3/1995 | WIPO . |
| WO 95/09866 | 4/1995 | WIPO . |
| WO 96 40739A | 12/1996 | WIPO . |

OTHER PUBLICATIONS

Jedlitschky, G. et al., "ATP–dependent Transport of Glutathione S–Conjugates by the Multidrug Resistance–associated Protein," *Cancer Research* 54, 4833–4836 (Sep. 15, 1994).

Lyttle, M.H. et al., "Glutathione–S–transferase Activities Novel Aklylating Agents," *J. Med. Chem.* (1994) 37:1501–1507.

Fenselau, C. et al., "High–performance tandem mass spectrometry in metabolism studies," *Xenobiotica* (1992) 22(9/10):1207–1219.

Sharer, J. E. et al., "Formation, Stability, and Rearrangements of the Glutathione Conjugates of Butadiene Monoxide: Evidence for the Formation of Stable Sulfurane Intermediates," *Chem. Res. Toxicol.* (1991) 4(4):430–436.

Akerboom, Th.P.M., et al., "Low– and high–Km transport of dinitrophenyl glutathione in inside of vesicles from human erythrocytes," *Biochem Biophys Acta* (1992) 1103(1):115–119.

Satiam, A., et al., "Design, Synthesis and Evaluation of Latent Alkylating Agents Activated by Glutathione S–Transferase," (1996) 39:1796–1747.

Bundgaard, H. "Design of Prodrugs" (1985) Elsevier Science Publishers B.V. pp. 1–24.

Silverman, R.B. "The Organic Chemistry of Drug Design and Drug Action" (Academic Press Inc. 1988) pp. 352–401.

*Primary Examiner*—Cecilia J. Tsang
*Assistant Examiner*—Bennett Celsa
*Attorney, Agent, or Firm*—Morrison & Foerster LLP

[57] ABSTRACT

Compounds wherein a biologically active molecule is coupled to a glutathione analog through a conjugated system which permits activation of the biologically active molecule while retaining the biologically active molecule tethered to the glutathione analog are useful as tethered prodrugs that slow the rate of clearance of an active biomolecule through the multidrug resistance pump.

6 Claims, 4 Drawing Sheets

TETHERED PRODRUGS

TECHNICAL FIELD

The invention relates to drug delivery systems, in particular, prodrugs that depend on glutathione S-transferase (GST) for activation. In particular, the invention concerns prodrugs wherein the active form of the drug resists clearance through the multidrug resistance associated protein (MRP) system by virtue of retained association with an analog form of glutathione.

BACKGROUND ART

PCT application WO 95/09866 published 13 Apr. 1995 and incorporated herein by reference, discloses a group of GST-activated compounds which rely on interaction of a prodrug form of a drug or toxin with glutathione S-transferase and the resulting abstraction of a proton by the enzyme, releasing an electron pair which mediates, in turn, the release of the drug or toxin. These compounds are generally of the following formula, where the pathway of released electrons from hydrogen ion abstraction is indicated.

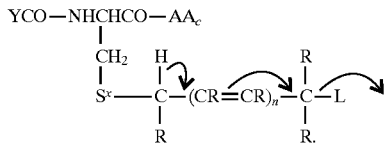

In these compounds,

L is an electron withdrawing leaving group;

$S^x$ is an oxidized form of S, Se or C, e.g., S=O, O=S=O, S=NH, HN=S=O, Se=O, O=Se=O, Se=NH, HN=Se=O, $S^+R'$ wherein R' is alkyl (1–6C) or O—C=O or HN—C=O;

each R is independently H or a noninterfering substituent;

n is 0, 1 or 2,

YCO is selected from the group consisting of γ-Glu, β-Asp, Glu, Asp, γ-GluGly, β-AspGly, GluGly and AspGly; and $AA_C$ is an amino acid linked through a peptide bond to the remainder of the compound.

As explained in the above-cited PCT application, specificity with respect to particular tissues or targets can be manipulated, mainly through appropriate choices for $AA_C$, and to a lesser extent, YCO. The reason for this is that the nature of the glutathione analog portion of the prodrug determines which of the many isozymes of GST are effective in releasing the biologically active moiety. The nature of the leaving group will determine the biological effect of administering the prodrug. Included among the leaving groups described are nitrogen mustards and other cytotoxic substances, as well as various antibiotics, indicator molecules, and other groups.

Although the prodrugs described in the PCT application are effective, they may also be cleared more quickly than desired from the target cells or tissue by virtue of elevated levels of multidrug resistance associated protein (MRP) which transports GSH-conjugated substances out of the cell as described by Jedlitschky, G. et al., *Cancer Research* (1994) 54:4833. For example, in the case of the phosphoramide mustards, displacement of a chloride ion from one of the 2-chloroethyl groups by the sulfhydryl group of glutathione results in a GSH-conjugate which can then be cleared by the MRP system.

It would be desirable to provide prodrugs which not only release active forms of the drugs per se, but also result in a lowered rate of clearance of the activated drug. The present invention provides two approaches to this problem. One approach resides in selecting, as the glutathione analog in the prodrug, a glutathione analog that itself interacts with the MRP, e.g., in competition with GSH. Thus, after the prodrug is cleaved by GST, the glutathione analog can inhibit the transport of other moieties, such as the activated drug or toxin. This approach is workable, however, only where the specificity desired for the prodrug release permits this choice to be made.

In a more universal approach, the prodrug is designed to activate, but not to release completely the biologically active moiety associated with it; the biologically active moiety remains tethered to the glutathione analog, reducing its susceptibility to GST-mediated conjugation to free GSH. Thus, it has reduced ability to form a compound which is effectively cleared by the MRP system.

DISCLOSURE OF THE INVENTION

The invention provides an improvement in the design of certain prodrugs, permitting lower dosages by virtue of inhibiting the rate of clearance of the activated drug. The prodrugs are designed so as to interfere with the clearance of the activated drug through the MRP efflux system.

Thus, in one aspect, the invention is directed to a method to enhance the effectiveness of prodrug administration, which method comprises assessing a panel of candidate glutathione analogs for their ability to interact with the MRP system;

selecting from said panel an analog which interacts with said MRP system;

synthesizing a prodrug which is a conjugate of the appropriate form of the selected analog with a substance of the desired biological activity; and administering the resulting prodrug to a subject in need of treatment with the biologically active compound.

In another aspect, the invention is directed to compounds of the formula:

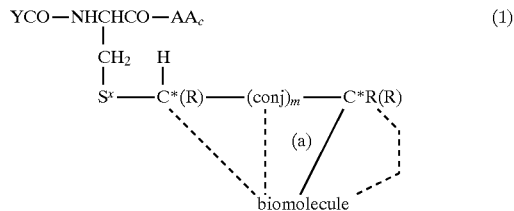

wherein $S^x$ is S=O, O=S=O, S=NH, HN=S=O, Se=O, O=Se=O, Se=NH, HN=Se=O, $S^+R'$ wherein R' is alkyl (1–6C), or $S^x$ is —O—C=O or —HN—C=O;

YCO is selected from the group consisting of γ-Glu, β-Asp, Glu, Asp, γ-GluGly, β-AspGly, GluGly and AspGly; and $AA_C$ is an amino acid linked through a peptide bond to the remainder of said compound of formula (1);

(conj) is a conjugated system permitting transfer of electron pairs, such as —CR=CR—; —(CR=CR)$_2$— or —phenylene—;

m is 0 or 1; each R is independently H or noninterfering substituent;

the dotted lines represent alternative covalent bonds tethering the biomolecule to the indicated C; and "biomolecule" represents a moiety which is biologically active when covalent bond (a) is severed.

Thus, one and only one covalent bond will be present among the group consisting of the dotted line linking biomolecule to C*, the dotted line linking biomolecule to C⁺ and the dotted line linking the biomolecule to a carbon in the conjugated system, if present.

Thus, in the compounds of formula (1), when the hydrogen ion α to $S^x$ is abstracted, releasing electrons (through the conjugated system, if present) ultimately to sever covalent bond (a), the "biomolecule" or portion thereof becomes biologically active, although it remains tethered to the remainder of the molecule either by covalent linkage to C* or by covalent linkage to C⁺or by covalent linkage to a carbon in the conjugated system if present. The nature of the coupling through covalent bond (a) of the biomolecule to the remainder of the compound of formula (1), i.e., the atom of the biomolecule that participates in the covalent bond is dependent on the nature of the biomolecule.

In one embodiment, the biomolecule contains a phosphoramidate mustard. In this embodiment, preferred are compounds of the formula

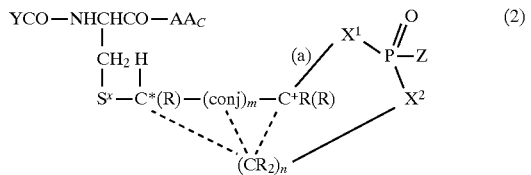

wherein $S^x$, YCO, $AA_C$, (conj), m, and R are defined as above;

n is an integer of 0–4;

each X is independently O, NH or S;

Z is a moiety which, when associated with $P(O)X^1X^2$ is biologically active; and the dotted lines represent alternative covalent bonds linking $CR_2$ and thus $X^2$ to the remainder of the molecule—i.e., to C*, C⁺, or a carbon in the conjugated system if present.

In another set of preferred embodiments, the compounds of the invention are of the formula

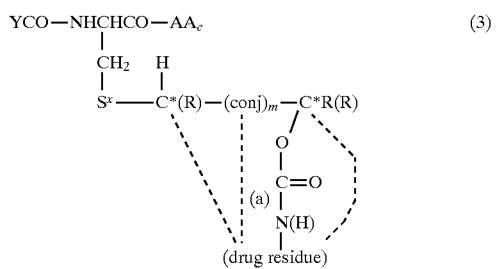

wherein $S^x$, YCO, $AA_c$, (conj), m, and R are defined as above, and "drug residue" represents a moiety which, when inclusive of the N(H) shown adjacent to it, is a biologically active drug. (In some drugs including those represented as illustrations herein, the N is in a 2° amino form, for example as a member of a heterocyclic ring, and thus no H should be shown. For illustration, the formulas herein display N(H) since H would be present if N is a 1° amino in the drug.) As in the formulas set forth above, the dotted lines represent alternative tethering covalent bonds to link the drug residue to the remainder of the molecule, either to the C*, C⁺, or a carbon of the conjugated system if present.

Again, the location of the tethering covalent bond in the drug residue is determined by the nature of the drug residue. When the covalent bond (a) is severed, the (drug residue)—$NH_2$ or (drug residue)—NH in the case of secondary amines, becomes biologically active and remains tethered to the remainder of the molecule through one and only one of the dotted alternative covalent bonds shown.

In all of the above formulas (R) indicates that R will be present when the dotted line covalent bond is absent and absent when the covalent bond represented by the dotted line is present.

In other aspects, the invention is directed to pharmaceutical compositions containing the compounds of formula (1) and to methods of modulating the metabolism of target cells by administering the compounds of formula (1) or pharmaceutical compositions thereof.

MODES OF CARRYING OUT THE INVENTION

Figure 1:
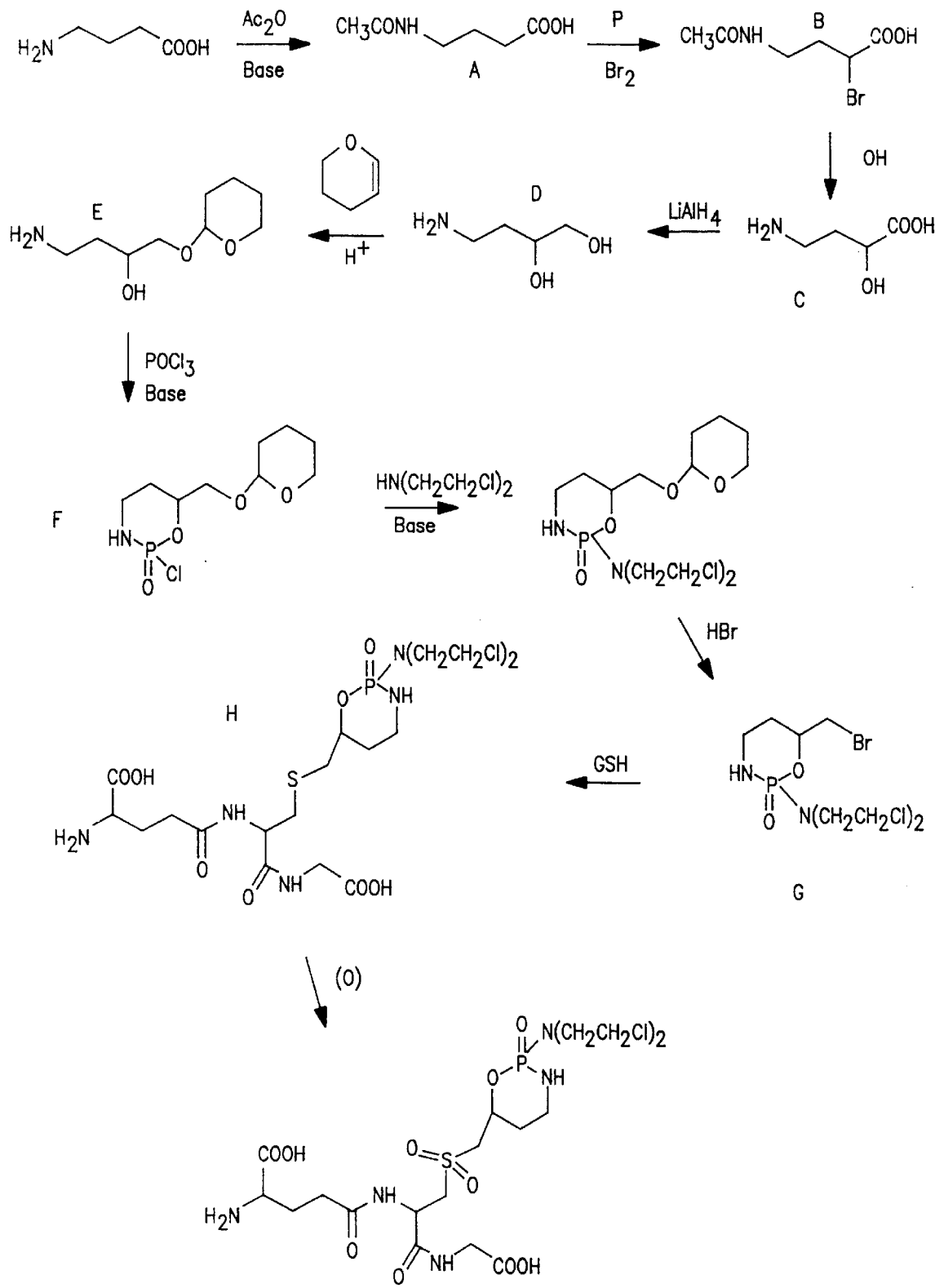
FIG. 1 shows a reaction scheme for the synthesis of some of the embodiments of the general formula (1) that are of the more specific formula (2), wherein $X^2$ is NH.

The compounds of formula (1) are prodrugs which can be used selectively to target tissues having GST complements which are elevated or which are peculiar in specificity to the prodrug provided. The specificity of the prodrug with respect to elevated classes of GST isoenzymes can be determined by appropriate choices of YCO and $AA_C$. Thus, these prodrugs, in addition to being selective for cells with elevated GST complements per se, can be used in a finely tuned protocol to target cells which have elevated levels of a particular isoenzyme of the GST group.

In addition to selectivity, the prodrugs of the invention are able to resist efflux of the activated drug from the target cells, thus permitting lower dosages of the prodrug. Resistance to efflux may also be obtained by selecting YCO and $AA_C$ in the prodrugs disclosed in WO 95/09866 so that the liberated glutathione analog (i.e., YCO—NHCH($CH_2S^x$—CH=$CH_2$)CO—$AA_C$) interacts with the MRP system to inhibit its ability to secrete additional substances when selectivity conditions permit such design choices. However, resistance to efflux may also be obtained by supplying the prodrugs of the present invention of formula (1), wherein the activated drug or other biologically active molecule remains tethered to the oxidized glutathione analog, typically a vinyl sulfone.

METHOD OF SELECTING EFFLUX RESISTANT PRODRUGS

The prodrugs described in the above-incorporated WO 95/09866 can be used directly to provide biologically active agents to target tissues if the specificity required for the target permits the appropriate choices of YCO and $AA_C$ so that the glutathione analog represented by the vinyl (typically) sulfone liberated when the biologically active agent is released interacts with the MRP clearance system so as to inhibit the ability of the system to effect clearance of the released biological moiety. Thus, for example, the glutathione analogs TER 106 (γGlu-C(Bz)-βAla); TER 222

(γGlu-C(Bz)-Gly); and TER 117 (γGlu-C(Bz)-ɸGly) have been assessed for their ability to interact with the MRP pump in assays described by Akerboom, et al. *Biochim Biophys Acta* (1992) 1103:115–119 and as described in Example 1 below. The results show that TER 222 and TER 106 interact with MRP so as to reduce the transport of radiolabeled GSH analog through the protein pump. However, TER 117 does not. A prodrug constructed from TER 117 as described in the above-referenced PCT application, TER 286, has the desired isoenzyme specificity for cells having GST complements high in the P1-1 isoform; however, this form of the prodrug would not advantageously inhibit efflux. On the other hand, prodrugs constructed from TER 222 and TER 106, provided the GST specificity is appropriate for the target tissue, could reasonably be used.

Thus, one aspect of the present invention is concerned with a method of enhancing the effectiveness of prodrug administration by first assessing the ability of glutathione analogs that can be incorporated in oxidized form into the classical prodrug constructs described in the above-referenced PCT application to select an analog that interacts with MRP. Methods similar to those described in Example 1 could, for example, be used. The successful candidate, which does exhibit interaction, is then used to synthesize the appropriate prodrug, provided the specificity conferred on the prodrug by the analog is consistent with the determined GST complement of the target cell. The designed prodrug is then administered to a subject in need of the biologically active agent contained in the prodrug.

TETHERED PRODRUGS

It may be difficult to find a glutathione analog which has both the ability to interact with the MRP clearance system and to confer the appropriate specificity on the prodrug. A more universally applicable method of ensuring both the required specificity and the efflux inhibition is the use of the tethered prodrugs of formula (1). In these compounds, the glutathione analog portion can be chosen on the basis of its specificity-conferring properties, and the biologically active moiety, because it remains tethered to the prodrug, although activated by partial release, is itself resistant to transport by the MRP pump, since the GSH moiety in this configuration is a poor substrate for the MRP pump.

The compounds of the invention of formula (1) are comprised of a tripeptide which is a glutathione analog coupled to a tethered leaving group through a molecular system which permits release of one of the bonds of the leaving group when the compound of formula (1) is treated with the appropriate GST. The release occurs through a "β-elimination"—i.e., the removal of the proton on the carbon α to the electron-poor carbon, sulfur or selenium releases electrons which are ultimately absorbed by an electronegative atom in the biomolecule. This can be shown schematically as follows:

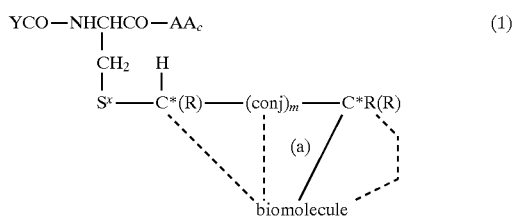

As shown, the electrons contained in covalent bond (a) are released into the biomolecule. However, the biomolecule remains tethered to the remainder of the molecule either through C*, C+, or a carbon contained in the conjugated system if present. Thus, compounds of formula (1') result:

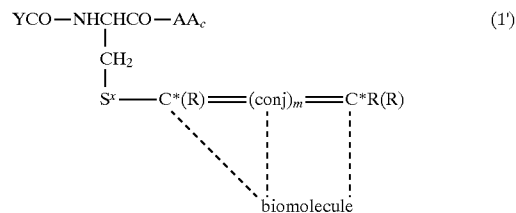

Because of the release of electrons into the biomolecule and severing covalent bond (a), the biomolecule becomes biologically active. However, because the biomolecule remains tethered to the remainder of the glutathione analog as shown, it is resistant to clearance systems associated with the multidrug resistance associated protein.

A specific instance of this release is shown for one embodiment of the compounds of formula (2a) below:

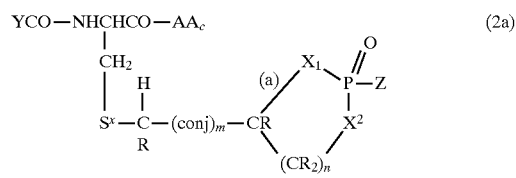

The electron pair can be released to $X^1$ adjacent to the P atom directly through β-elimination as shown above or through a system of conjugation represented by $(conj)_m$ in formula (1). Thus, theoretically any number of conjugated π bonds may be included in (conj) but the efficiency of the electron transport is believed to decline as this number increases.

After activation by the appropriate GST, the resulting molecule is an activated biologically active moiety wherein the biologically active portion is tethered to the glutathione analog as shown in formula (2a')

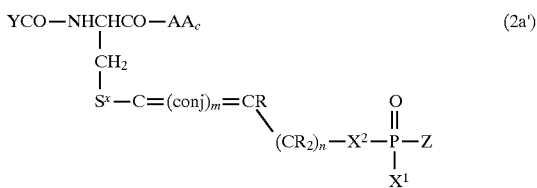

Because the partial release exposes the entity $P(O)X^1X^2$—z, this moiety can now provide biological activity.

Suitable embodiments for Z include those which generate drugs which may be cytotoxic to unwanted cells. Such drugs include the phosphoramidate mustards. Preferred forms of the phosphorodiamidate mustards are —OP(O)(N(CH$_2$CH$_2$Cl)$_2$)$_2$, —OP(O)(N(CH$_2$CH$_2$Br)$_2$)$_2$, —OP(O)(NHCH$_2$CH$_2$Cl)$_2$ and —OP(O)(NHCH$_2$CH$_2$Br)$_2$; thus, in these cases $X^1$ is identical to Z in formula (2a'). However, compounds wherein Z is, e.g., N(CH$_2$CH$_2$Cl )$_2$ and $X^1$ is O are also preferred.

Because the mustards remain tethered to the glutathione analog as shown above, they are unlikely to react with glutathione per se in the conventional manner, wherein a chloride ion is released from the 2-chloroethyl moiety to couple glutathione directly to the drug. Steric interference in the GST active site by the conjugated GSH will diminish the opportunity for a free GSH to be coupled to the phosphoramidate for efflux in the pump. Thus, absent this coupling, they cannot be transported out of the cell using the MRP clearance pathway.

Another embodiment of the compounds of the invention is illustrated by those of formula (3).

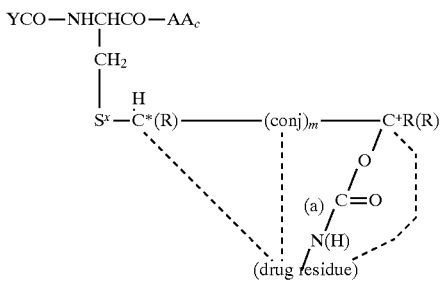

(3)

As above, the release of electrons liberated by abstraction of the proton a to SX results in the release of $CO_2$ and the lysis of the C—N bond (a) of the carbamoyl moiety leaving the electron pair associated with the nitrogen included in the drug. Accordingly, the biologically active drug remains associated with the remainder of the molecule through $C^*$, $C^+$ or through a carbon of the conjugated system as above. In one typical embodiment, the resulting molecule will be of the formula

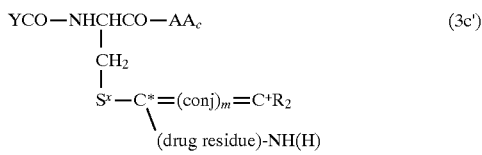

(3c')

As explained above, the number of H associated with the carbamoyl N will depend on whether, in the drug, the N is part of a 1° or 2° amine.

Suitable embodiments of the "drug residue—NH" include nitrogen-containing antibiotics such as dynemycin-A and mitomicin-C. Thus, typical embodiments of the invention involving these pharmaceutically active compounds would include:

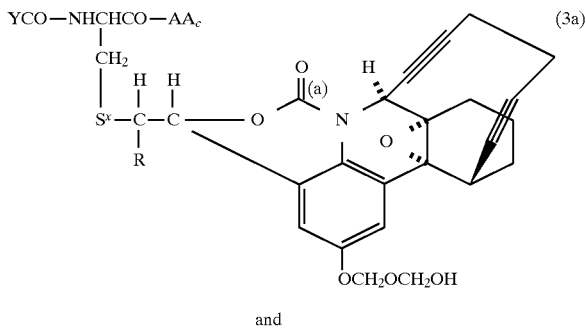

(3a)

and

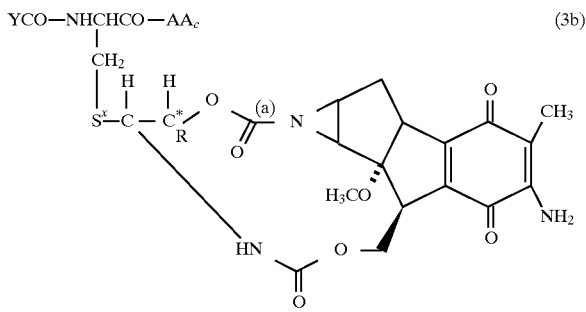

(3b)

It will be seen that the compounds of formula (3) are characterized by including the amino group of a drug in a carbamoyl linkage to a glutathione analog. The covalent bond (a) of the carbamoyl is cleavable by electron donation originating from abstraction of a proton adjacent to $S^x$, liberating $CO_2$. A second covalent bond originating elsewhere in the drug and attached to $C^*$, $C^+$, or a carbon in the conjugated system, if present, tethers the (drug residue)—NH to the glutathione analog. Depending on the nature of the drug, the points of attachments will be determined as would be understood by those of ordinary skill.

The structural requirements for the prodrugs of the invention are outlined above.

The R substituents play no direct part in the release of electrons to the biomolecule and simply must be noninterfering substituents. The rate of β-elimination can, however, be controlled by the nature of these R groups; by choosing electron withdrawing or electron donating substituents the rate of elimination can be accelerated or decreased. Suitable substituents for R include H, substituted or unsubstituted alkyl (1–6C) substituted or unsubstituted aryl (6–12C), substituted or unsubstituted aryl alkyl (7–12C), cyano, halo, substituted or unsubstituted alkoxy (1–6C), substituted or unsubstituted aryloxy (6–12C) or substituted or unsubstituted arylalkyloxy (7–12C).

Alkyl, aryl, and arylalkyl have their conventional meanings; alkyl groups are straight, branched chain or cyclic saturated hydrocarbon moieties such as methyl, tert-butyl, cyclohexyl, and the like. Aryl groups include aromatic systems such as phenyl, naphthyl, pyridyl and the like. Arylalkyl substituents contain an aryl moiety coupled to the remainder of the molecule through an alkylene moiety. Such groups include, most commonly benzyl, phenylethyl, 2-pyridylethyl, and the like.

Suitable substituents in the substituted forms include halo, SR", OR", and $NR_2'$ wherein R" is H or lower alkyl (1–4C).

Preferred embodiments for each R independently are H, lower alkyl (1–4C) and phenyl, especially H or lower alkyl (1–4C). In particularly preferred embodiments, R is H and m=0. However, any noninterfering substituents may be used as R; these substituents are independently embodied.

The embodiments of YCO and —$AA_C$ determine the nature of the glutathione-like tripeptide. A preferred embodiment is that wherein YCO is γ-glutamyl and $AA_C$ is glycine, phenylglycine, β-alanine, alanine or phenylalanine, resulting in the tripeptide glutathione or a close analog. However, alternative embodiments of YCO include β-Asp, Glu, Asp, γ-GluGly, β-AspGly, GluGly and AspGly. Alternative embodiments of AAC include, along with the preferred glycine, phenylglycine, β-alanine, alanine, and unsubstituted phenylalanine: valine, 4-aminobutyric acid, aspartic, phenylglycine, histidine, tryptophan, tyrosine, and substituted phenylalanine. Suitable phenylalanine substituents are as described above for the substituted forms of R.

The compounds of the invention may also be prepared in the forms of their esters or amides, mixed ester/amides or as the salts. The esters, amides or salts are formed with any or all carboxyl groups present in the molecule; hence, included in this group are monoesters, diesters, and, if applicable, triesters. Similarly, monoamides, diamides, or, if applicable, triamides are included. Mixed ester/amides are also part of the invention.

The esters or amides may be alkyl (1–6C), alkenyl (1–6C) or arylalkyl (7–12C). Alkyl esters of the free carboxyls are esters of the straight- and branched-chain alkyl alcohols (1–6C) such as methanol, ethanol, isopropanol, t-butanol, n-hexanol and the like. Suitable alkyl (1–6C) amides are those of primary straight- or branched-chain alkyl amines, such as methylamine, ethylamine, n-propylamine, isopentylamine, and isohexylamine. Alkenyl esters are similar, but contain at least one double bond. Arylalkyl is as defined above. The alcohols or amines may also carry noninterfering substituents such as halo, alkoxy, or alkyl amines. The esters and amides are prepared using conventional techniques, with suitable protection of any alcohol or amino functional groups in the compound of formula (1).

The salts of the compounds of the invention may be formed of inorganic or organic bases to form the basic salts of the free carboxyl groups or may be formed from organic or inorganic acids to obtain the acid addition salts of free amino groups. Thus, the salts may be of inorganic bases such as sodium hydroxide, potassium hydroxide, calcium hydroxide, ammonium hydroxide, magnesium hydroxide, and the like, or of organic bases such as trimethylamine, pyridine, pyrimidine, piperidine, lysine, caffeine, and the like. The acid addition salts may be formed from inorganic acids such as hydrochloric acid, hydrobromic acid, sulfuric acid, phosphoric acid, and the like, or from organic acids such as acetic acid, propionic acid, glycolic acid, pyruvic acid, oxalic acid, malic acid, tartaric acid, citric acid, benzoic acid, cinnamic acid, mandelic acid, salicylic acid, and the like. Salts of citric acid are preferred.

The salts of the compounds of formula (1) are formed in standard protocols by treating with the appropriate base or acid at a temperature of from about 0° C. to about 100° C., preferably at room temperature either in water alone or in combination with an inert water-miscible organic solvent such as methanol, ethanol or dioxane.

Preferred forms of the compounds of formula (1) are those wherein $S^x$ is $S=O$, $O=S=O$, $S=NH$, $HN=S=O$, $Se=O$, $O=Se=O$, $Se=NH$, $HN=Se=O$, $S^+R'$ wherein R' is alkyl (1–6C), more preferably wherein $S^x$ is $O=S=O$ or $S=O$, particularly $O=S=O$. Also preferred are those compounds wherein m=0 and all R substituents are H. Particularly preferred embodiments of formula (1) are those represented by formulas (2) and (3). Particularly preferred among compounds of formula (2) are those wherein Z is $N(CH_2CH_2Cl)_2$ or $NHCH_2CH_2Cl$ or the analogs containing Br in place of Cl. A particularly preferred embodiment of n is 2. A particularly preferred embodiment of $X^1$ is O and of $X^2$ is O or NH or $NCH_2CH_2Cl$ or $NCH_2CH_2Br$. Especially preferred are compounds of the following formulas:

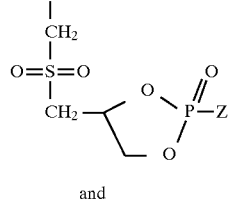

and

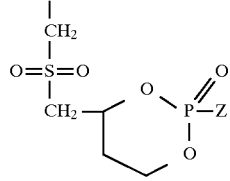

wherein YCO is γGlu and $AA_C$ is phenylglycine, glycine, or β-alanine, and Z is $N(CH_2CH_2Cl)_2$ or $NHCH_2CH_2Cl$ However, the selection of YCO and $AA_C$ can be widely varied within the definition set forth above to confer the "appropriate specificity" on the prodrug.

Preferred embodiments of the compounds of formula (3) are of the formula

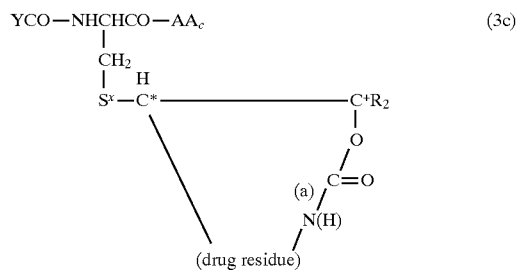

wherein $S^x$ is $O=S=O$, and in particular where the (drug residue)—N represents mitomycin-C or dynemycin-A. Particularly preferred are the compounds of formulas (3a) and (3b) set forth above wherein YCO is γ-Glu and $AA_C$ is phenylglycine, glycine or β-alanine.

As above, the selection of YCO and $AA_C$ can be varied to confer appropriate specificity on the prodrug.

USE OF THE INVENTION COMPOUNDS FOR TARGETED DRUG DELIVERY

In one aspect the invention provides a vehicle for delivering drugs to tissues specifically based on their GST content wherein efflux via MRP is diminished. The biologically active agent, when partially released in the target tissue will exert its desired effects selectively in that target tissue. The target cells where the partial release will occur can be regulated by manipulating the nature of the glutathione analog portion of the molecule.

As described above, the various tethered prodrugs of the invention are selective for the various isozymes of GST whose levels may be elevated in tumor cells. As with the prodrugs described in WO 95/09866, by determining the profile of GST isoenzyme levels in the tumor target, and matching this with the specificity of the prodrug, maximum effectiveness against the tumor cell will be obtained and maximum selectivity for the tumor cell as opposed to normal tissue can be achieved. The selectivity of the prodrug depends to a significant extent on the choice of the glutathione analog used as a component of the drug.

In illustrative compounds described in the PCT application, TER 231 is especially susceptible to cleavage by GST M1a-1a; TER 303 is especially susceptible to cleavage by A1-1; TER 286 is particularly susceptible to cleavage by P1-1 and A1-1, while TER 296 is selectively cleaved by P1-1. Thus, in treating a tumor having elevated levels of P1-1, use of a compound of formula (1) having the tripeptide contained in TER 296 or TER 286 would be preferred. The relevant isoenzyme, GST P1-1 is elevated in more than 75% of human tumor specimens from breast, lung, liver and colon.

The appropriate choice of prodrug is also facilitated by determining the GST complement of the cells to be treated in comparison with normal tissues. Detailed instructions for obtaining such complements are found in PCT application US 92/03537 published in October of 1992. The description in this PCT application sets forth methods for determining which GST isoenzymes are elevated in particular tissues.

The compounds of formula (1) are administered as pharmaceutical compositions in usual formulations such as those outlined in *Remington's Pharmaceutical Sciences,* Mack Publishing Company, Easton, Pa., latest edition. Typical formulations will include those for injection, for transdermal and transmucosal administration, and for oral administration. The formulations, depending on the intended mode, may be liquids, syrups, powders, capsules, suppositories, and the like. The compounds of the invention may be included in liposomes, or in other emulsified forms. Protocols for administration and suitable formulations are subject to optimization using standard procedures known to those in the art.

The antitumor activity of the invention compounds of formula (2) coupled with phosphorodiamidate mustard or other toxins can be assessed using a number of human tumor xenografts to determine tumor growth inhibition or a B16 mouse melanoma and measuring the prolongation of survival to determine the efficacy of particular compounds.

The compounds of the invention in general will be administered with respect to the appropriate indication for the biomolecule. Thus, for treatment of infections, embodiments wherein the biomolecule contains a moiety with antibiotic activity will be employed; for antitumor indications, chemotherapeutic agents will be included in the biomolecule; and the like. Suitable indications will depend on the nature of the moiety contained within the biomolecule as is understood by the skilled practitioner. The clearance systems described operate, not only in mamalian systems, but in living systems in general. Thus, an appropriate biologically active compound can be administered to any suitable recipent subject, including insects, parasites, or plants. The choice of biomolecule will depend on the nature of the intended effect and the nature of the subject.

SYNTHESIS OF THE INVENTION COMPOUNDS

The compounds comprising glutathione or its analogs described above coupled to a desirable biologically active moiety can be synthesized using means generally known in the art. Where $S^x$ is an oxidized form of S or Se, the methods illustrated below can be used, incorporating modifications which render them applicable to desired compounds of the invention.

Thus, for example, compounds of formula (1) wherein $S^x$ is S=O, Se=O, O=S=O or O=Se=O can be produced from the corresponding compounds wherein S or Se is in reduced form by oxidation with mild oxidizing agents such as peroxide or peracetate. Compounds of formula (1) wherein $S^x$ is S=NH, Se=NH, O=S=NH, or O=Se=NH can be obtained by treatment of the appropriate precursor having reduced S or Se, or a partially oxidized form, with chloramine T under conditions known in the art. Alternatively, the method of Whitehead, J.K. et al., *J Chem Soc* (1952) 1572–1574, may be used. Dipeptide precursors can be converted to the compound of formula (1) by coupling the YCO moiety or the $AA_C$ amino acid to the appropriate dipeptide using standard peptide coupling techniques. When S or Se are in reduced form in the dipeptide, these compounds may, similarly, be converted to tripeptides with S or Se reduced. Compounds of formula (1) wherein $S^x$ is a sulfonium ion, i.e., is $S^+$; may be synthesized by treating compounds with reduced S with alkyl halides under suitable conditions to alkylate the sulfide, or intermediates can be synthesized from corresponding dipeptide compounds. R' is alkyl (1–6C) as defined above. Preferred alkyl halides for reaction to form, ultimately, compounds of formula (1) in this embodiment are the iodides.

For compounds of formula (1) wherein $S^x$ is O—C=O are obtained using as a dipeptide or tripeptide starting material analogs of glutathione wherein serine substitutes for the cysteine moiety. Compounds are then obtained by esterification of the di- or tripeptide containing serine. Where $S^x$ is NH—C=O, the corresponding amidation reaction is effected with analogs wherein 2,3-diaminopropionic acid replaces cysteine.

Shown in FIG. 1 is a sequence of reactions to obtain the precursor to the embodiment wherein $S^x$ is O=S=O for compounds of formula (2) where $X^2$ is NH. The sulfone is obtained from the sulfur in reduced form by treating with mild oxidizing agents as described above, such as peracetic acid.

The last step in the reaction sequence prior to oxidation to the sulfone is coupling of the glutathione analog to a brominated form of the tethered moiety. The construction of the tethered moiety is as follows: The starting material, 4-aminobutyric acid, is first acetylated in acetic anhydride and base such as pyridine or triethylamine to give Compound A. The bromine a to the carboxyl is introduced using Hell-Volhard-Zelinski conditions and the resulting compound is hydrolyzed in base to obtain Compound C, γ-amino-α-hydroxybutyric acid. Compound C is reduced with lithium aluminum hydride to obtain the diol D, which is treated with dihydropuran in the presence of an acid catalyst to provide the tetrahydropyranyl alcohol amine, E. Compound E is then treated with phosphorous oxychloride and base to obtain Compound F, which is purified by crystallization or chromatography. The isolated Compound F is then treated with bis-2-chloroethylamine and base, followed by reaction with HBr to give Compound G, which is isolated and reacted with a suitable glutathione analog to give the sulfide, H, under reductive alkylation conditions ($NaBH_4$, ammonia, inert atmosphere). Oxidation of compound H to the desired compound of formula (2) with peracetic acid is followed by purifying the product with HPLC.

Figure 2:
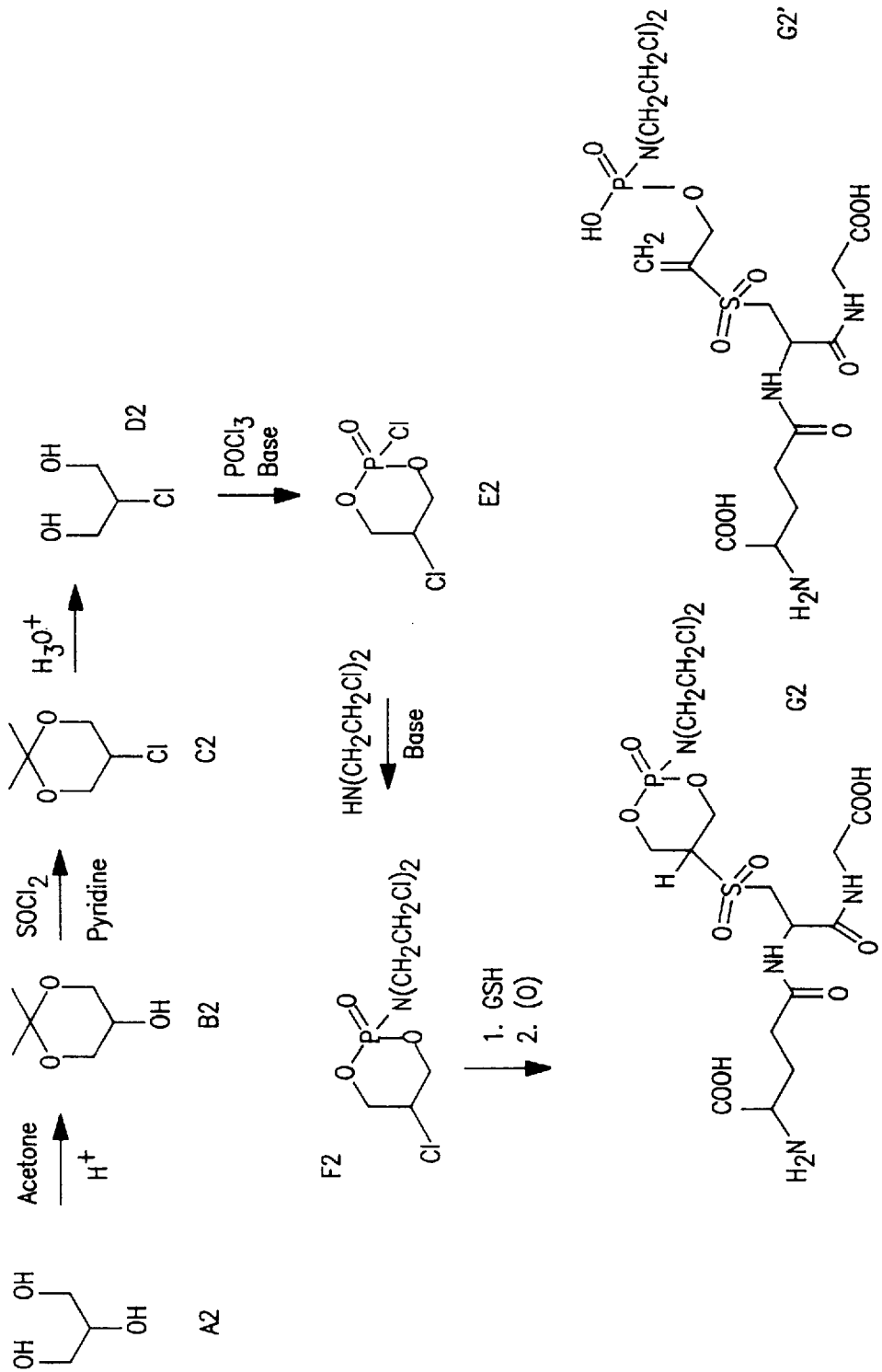
FIGS. 2 and 3 show reaction schemes for syntheses of compounds of formula (2) wherein $X^2$ is O.
Figure 3:
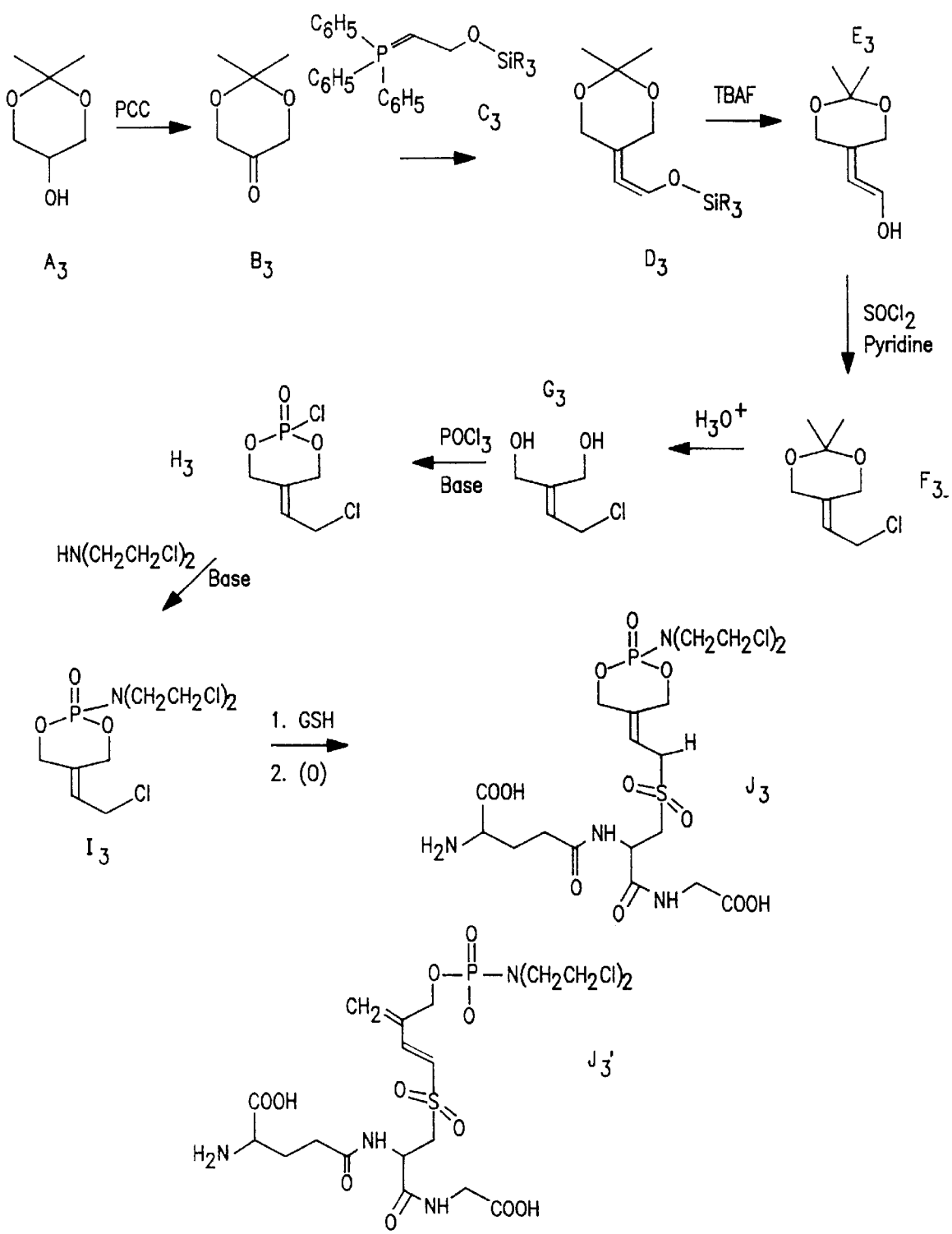

FIGS. 2 and 3 show the synthesis of alternative forms of the compounds of formula (2) wherein $X^2$ is O. In FIG. 2, glycerol (A2) is reacted with acetone under mildly acidic dehydrating conditions typified by Dean-Stark to give the corresponding ketal, the six-membered ring B2. Displacement of the ring hydroxyl with chloride using $SOCl_2$ in pyridine provides the resultant C2 which is then hydrolyzed under mildly acidic conditions to obtain 1,3-dihydroxy-2-chloropropane, D2. D2 is treated with phosphorus oxychloride to obtain the cyclic diester E2 which is then reacted with bis-(2-chloroethyl)amine in the presence of base, preferably triethylamine, to give F2. F2 is then reacted with the desired glutathione analog, such as GSH itself, under reducing conditions ($NH_4OH$, $NaBH_4$, argon) to provide the intermediate sulfide which is purified and oxidized to provide the compound of formula (G2). In G2 as shown, $S^x$ is O=SαO, $X^1$ and $X^2$ are both O, and Z is $N(CH_2CH_2Cl)_2$. In formula (G2), n is 1 and m is 0.

Also shown in FIG. 2 is the resultant G2' when the hydrogen α to the sulfone is abstracted and the prodrug is converted to the tethered active form.

FIG. 3 shows the synthesis of the analogous compound of formula (2), J3, wherein m=1. Release of the hydrogen ion a to the sulfone in J3 provides the tethered active form shown as J3'.

To synthesize J3, the ketal prepared in FIG. 2 is oxidized under anhydrous conditions using pyridinium chlorochromate (PCC) to obtain the corresponding ketone B3. B3 is then treated with Wittig reagent C3 to obtain the silylated conjugated compound D3. D3 is desilylated with tetrabutylammonium fluoride (TBAF) to obtain the allyl alcohol D2, which is then chlorinated with $SOCl_2$ in pyridine to obtain F3. The remaining steps are similar to those shown in FIG. 2. The ketal is hydrolyzed to give the diol G3 which is then treated with phosphorus oxychloride in the presence of base resulting in phosphorylation to obtain H3. H3 is then treated with bis-(2-chloroethyl)amine and base to give I3 which is then purified and then coupled to the desired glutathione analog under basic reducing conditions, as were set forth in FIG. 2 to provide the sulfide, which is then purified and oxidized to obtain J3, the final product.

Figure 4:
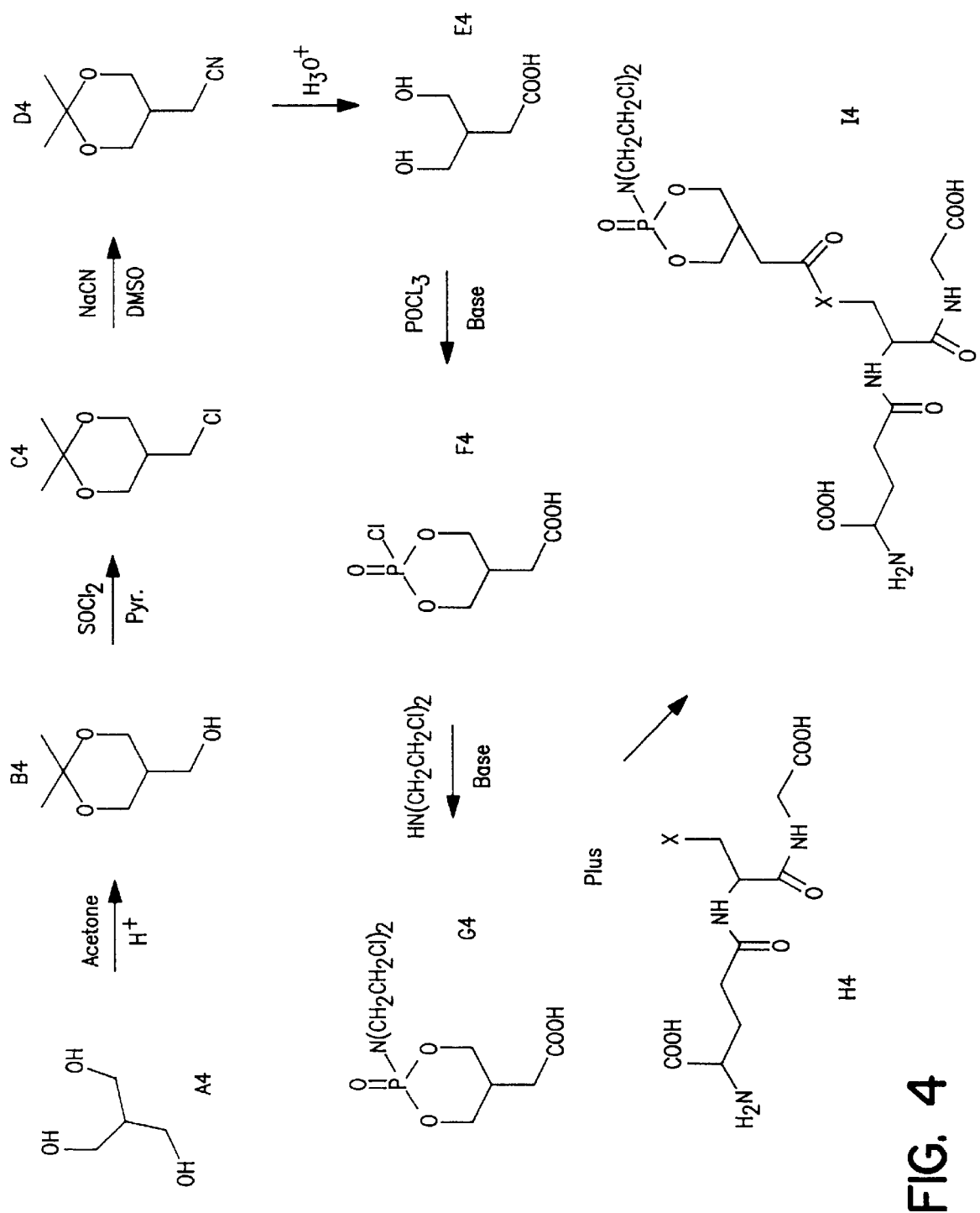
FIG. 4 shows the synthesis of compounds of formula (2) wherein $S^x$ is —O—C=O or —NH—O=CO.

FIG. 4 shows the synthesis of compounds of formula (2) wherein $S^x$ is —O—O=O or —NH—C=O. As shown in FIG. 4, the triol A4 is reacted with acetone under acidic dehydrating conditions to provide the ketal B4. B4 is chlorinated with thionyl chloride to give C4, which is converted to nitrile D4 with sodium cyanide. Hydrolysis of D4 affords E4, which is then phosphorylated to give F4. F4 is treated with bis-(2-chloroethyl)amine in the presence of base to obtain G4. G4 is reacted with the desired glutathione analog in which the position of the sulfhydryl is replaced with OH or $NH_2$ (shown as "X" in FIG. 4) to obtain the resulting ester- or amide-linked prodrug shown as I4. This coupling is effected by preforming an active ester of G4 with standard reagents such as dicyclohexylcarbodiamide or N-hydroxysuccinimide. During this step, the glutamic acid amine may be transiently masked using standard amino protecting groups such as t-BOC, for better control of the reaction. Abstraction of the hydrogen α to the carbonyl group in I4 results in the tethered active form (not shown).

The following examples are intended to illustrate but not to limit the invention.

EXAMPLE 1

Determination of the Interaction of Glutathione Analogs with MRP

Two indirect measures of interaction of test compounds in the MRP system of human erythrocytes were used. The first was stimulation of basal $Mg^{+2}$ stimulated ATPase activity, the other was inhibition of transport of tritiated dinitrophenyl-S-glutathione.

In the first method, the method of Bartosz, M. et al, *Biochem Mol Biol Int* (1994) 34:521–529 was used. Briefly, the compounds were added to erythrocyte membranes in a medium containing 100 mM Tris HCl, pH 4, 10 mM $MgCl_2$, 1 mM ATP, 0.1 mM ouabain and 1 mM EGTA with an incubation at 37° C. for 30 minutes. Stimulation of ATPase activity was measured as described.

In this assay, TER 117 did not stimulate ATPase activity. TER 222 stimulated this activity, resulting in a $V_{max}$ of 125.9 mM/mg protein per hr; $V_{max}$ observed for TER 106 was 209.6 mM/mg protein per hr; $K_m$ for TER 222 was 0.385 mM; for TER 106, 1.82 mM. The foregoing values were averages of three separate determinations.

In the alternative method, the uptake of tritiated DNP-glutathione conjugate by inside-out vesicles of human erythrocytes was determined as described in Akerboom, T. P. M. et al, *Biochim Biophys Acta* (1992) 1103.:115–119. The labeled DNP-GSH concentration was 5 μM and the compounds were added at a final concentration of 1 μM; uptake of labeled DNP-GSH was measured after 15 minutes incubation at 37° C. As a mean of three separate trials, TER 222 showed 62.5% inhibition of labeled conjugate uptake; TER 106 showed a 66.2% inhibition; and TER 117, 0.2% inhibition.

Thus, prodrugs containing TER 222 and TER 106 as the glutathione analog, provided the specificity for the GST complement of the target tissue is appropriate, can usefully be supplied, possibly without the necessity of tethering the biologically active agent.

EXAMPLE 2

Selective Activation of Phosphoroamidates by GST Isoenzymes

The selectivity of activation of the compounds of the invention is analogous to that described by Lyttle, M. H. et al, *J Med Chem* (1994) 37:1501–1507. Briefly, depending on the analog of glutathione used in the conjugate, selectivity is shown for GSTs of the isoforms A1-1, M1a-1a and P1-1. Determination of in vitro cytotoxicity of the compounds of the invention is conducted as described in this publication.

We claim:

1. A compound of the formula

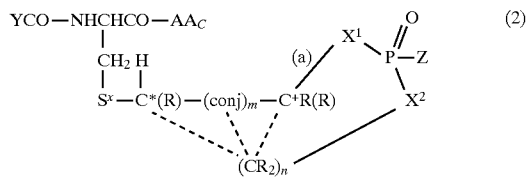

and the amides, esters, mixed ester/amides and salts thereof, wherein:

$S^x$ is S=O, O=S=O, S=NH, HN=S=O, Se=O, O=Se=O, Se=NH, HN=Se=O, $S^+R'$ wherein R' is alkyl (1–6C), or O—C=O or HN—C=O;

YCO is selected from the group consisting of γ-Gly, β-Asp, Glu, Asp, γ-GluGly, β-AspGly, GluGly and AspGly;

$AA_C$ is an amino acid linked through a peptide bond to the remainder of said compound of formula (1);

each R is independently H or a noninterfering substituent;

(conj) is a conjugated system;

m is 0 or 1;

n is an integer of 1–4;

each of $X^1$ and $X^2$ is independently S, O, or NH; and

Z is a moiety which, when associated with $P(O)X^1X^2$, results in a biologically active moiety which biologically active moiety is a tethered phosphoramide mustard or a tethered phosphorodiamidate mustard;

and wherein each of the dotted lines represents a covalent bond between $(CR_2)_n$ and $C^*$, $C^+$, or a carbon in the conjugated system if present with the proviso that one and only one said bond is present.

2. The compound of claim 1 wherein m=0; and/or wherein YCO is γ-glutamic acid; and/or wherein $AA_C$ is alanine, phenylalanine, glycine or phenylglycine; and/or wherein each R is independently H, lower alkyl (1–4C) or phenyl; and/or wherein Z is $N(CH_2CH_3)_2$, $N(CH_2CH_2Cl)_2$, $NHCH_2CH_2Cl$, $N(CH_2CH_2Br)_2$, or $NHCH_2CH_2Br$; and/or wherein $S^x$ is O=S=O.

3. The compound of claim 2 wherein each R is H.

4. The compound of claim 2 wherein $AA_C$ is phenylglycine.

5. The compound of claim 2 which has the formula

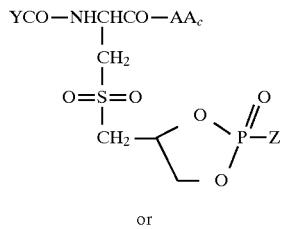 (2b)

or

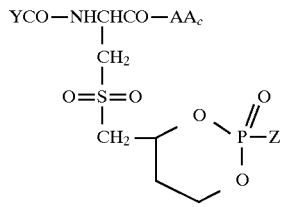 (2c)

wherein YCO is γGlu and AA$_C$ is phenylglycine, glycine, or β-alanine, and Z is N(CH$_2$CH$_2$Cl)$_2$ or NHCH$_2$CH$_2$Cl.

6. A compound for the preparation of the compound of claim 4 of the formula selected from the group consisting of:

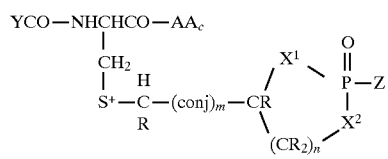 (a)

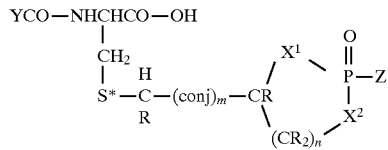 (b)

and

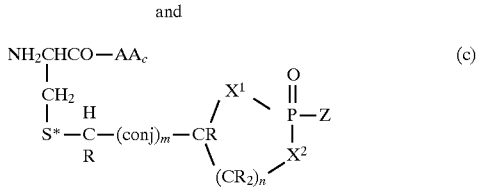 (c)

and the amides, esters, mixed ester/amides or salts thereof, wherein:

S* is S$^+$ or S$^x$;

S$^+$ is S or Se;

S$^x$ is S=O, O=S=O, S=NH, HN=S=O, Se=O, O=Se=O, Se=NH, HN=Se=O, S$^+$R' wherein R' is alkyl (1–6C), or S$^x$ is —O—C=O or —HN—C=O;

Y is selected from the group consisting of γ-Glu, β-Asp, Glu, Asp, γ-GluGly, β-AspGly, GluGly and AspGly;

AA$_C$ is an amino acid linked through a peptide bond to the remainder of said compound of formula (1);

each R is independently H or a noninterfering substituent;

m is 0 or 1;

n is an integer of 0–4;

each of X$^1$ and X$^2$ is independently S, O, or NR' wherein R' is H or a noninterfering substituent; and Z is a moiety which, when associated with P(O)X$^1$X$^2$, results in a biologically active moiety, which biologically active moiety is a tethered phosphoramide mustard or a tethered phosphorodiamidate mustard.

* * * * *